(12) United States Patent
Chen et al.

(10) Patent No.: US 10,279,372 B2
(45) Date of Patent: *May 7, 2019

(54) METHOD FOR FORMING A COATING ON A STENT

(71) Applicant: Abbott Cardiovascular Systems Inc., Santa Clara, CA (US)

(72) Inventors: Yung-Ming Chen, Cupertino, CA (US); Jason Van Sciver, Los Gatos, CA (US); Jeff McCabe, San Jose, CA (US); Antonio Garcia, San Jose, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 16 days.

This patent is subject to a terminal disclaimer.

(21) Appl. No.: 15/853,551

(22) Filed: Dec. 22, 2017

(65) Prior Publication Data

US 2018/0117625 A1    May 3, 2018

Related U.S. Application Data

(60) Continuation of application No. 14/479,080, filed on Sep. 5, 2014, now Pat. No. 9,849,481, which is a continuation of application No. 13/759,001, filed on Feb. 4, 2013, now Pat. No. 8,846,131, which is a division of application No. 12/027,947, filed on Feb. 7, 2008, now Pat. No. 8,367,150, which is a continuation-in-part of application No. 11/764,006, filed on Jun. 15, 2007, now Pat. No. 7,897,195.

(51) Int. Cl.
| | |
|---|---|
| *B05D 1/02* | (2006.01) |
| *A61F 2/91* | (2013.01) |
| *B05B 13/02* | (2006.01) |
| *B05B 13/04* | (2006.01) |
| *B05D 7/00* | (2006.01) |
| *B23K 26/402* | (2014.01) |
| *B23K 103/00* | (2006.01) |

(52) U.S. Cl.
CPC .............. *B05D 1/02* (2013.01); *A61F 2/91* (2013.01); *B05B 13/0228* (2013.01); *B05B 13/0442* (2013.01); *B05D 7/00* (2013.01); *B23K 26/402* (2013.01); *B23K 2103/42* (2018.08); *B23K 2103/50* (2018.08)

(58) Field of Classification Search
CPC .... B05D 1/02; B05D 7/00; B05D 1/44; A61F 2/91; B05B 13/0228; B05B 13/0442; B23K 26/402; B23K 2203/42; B23K 2203/50
USPC .................. 427/2.25; 118/57; 623/1.11, 1.42
See application file for complete search history.

(56) References Cited

U.S. PATENT DOCUMENTS

| | | | | |
|---|---|---|---|---|
| 7,897,195 | B2 * | 3/2011 | Rego ........................ | B05D 1/02 427/2.24 |
| 8,051,798 | B2 * | 11/2011 | Hossainy ............ | B05B 13/0442 118/320 |
| 8,367,150 | B2 * | 2/2013 | Chen ........................ | A61F 2/91 118/500 |

(Continued)

*Primary Examiner* — Andrew J Bowman
(74) *Attorney, Agent, or Firm* — Squire Patton Boggs (US) LLP

(57) ABSTRACT

A method for forming a coating on a stent involves spraying or drying a coating on the stent while the stent is supported on a mandrel assembly, during which part of the stent is made to go out of contact with the mandrel assembly.

12 Claims, 20 Drawing Sheets

(56) References Cited

U.S. PATENT DOCUMENTS

| | | | |
|---|---|---|---|
| 8,846,131 B2* | 9/2014 | Chen | A61F 2/91 427/2.14 |
| 9,849,481 B2* | 12/2017 | Chen | B05D 1/02 |
| 2003/0215564 A1* | 11/2003 | Heller | A61F 2/86 427/2.25 |
| 2007/0207186 A1* | 9/2007 | Scanlon | A61F 2/07 424/424 |

* cited by examiner

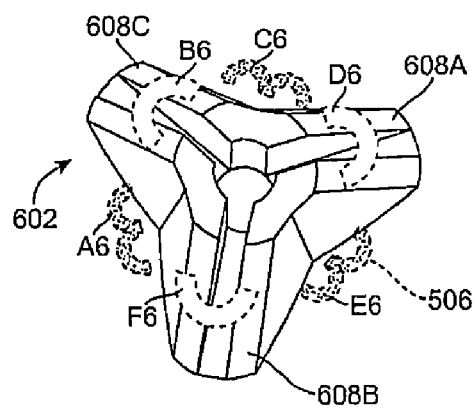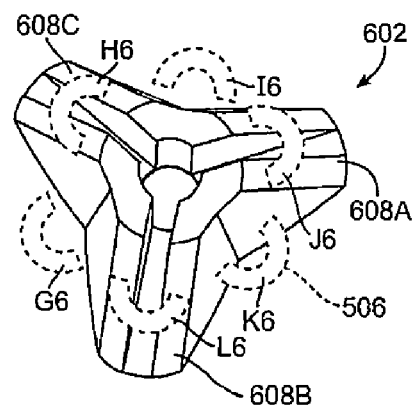
FIG.14A  FIG.14B
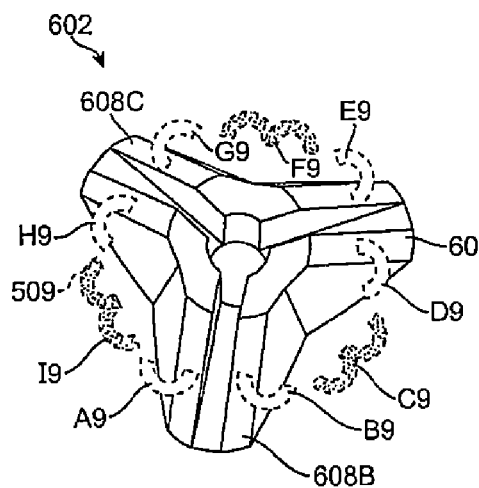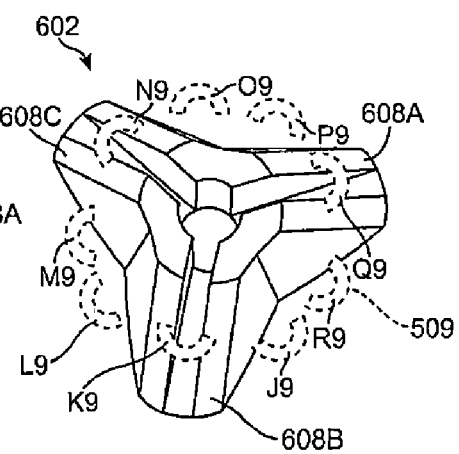
FIG.15A  FIG.15B

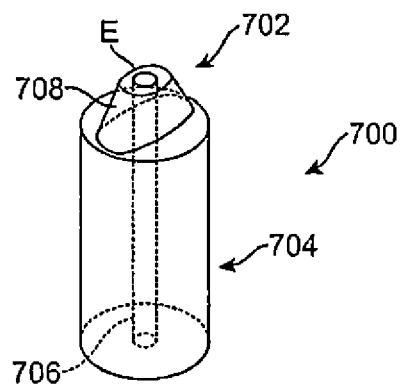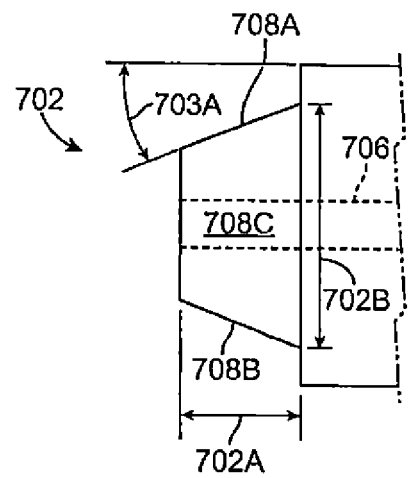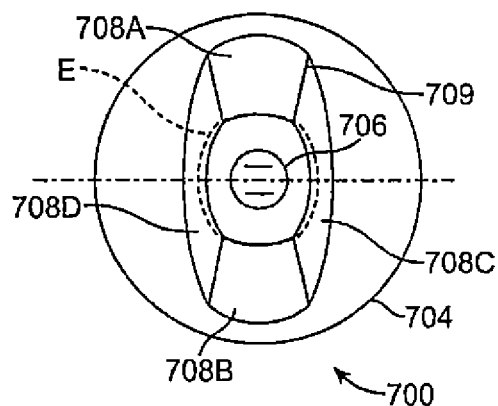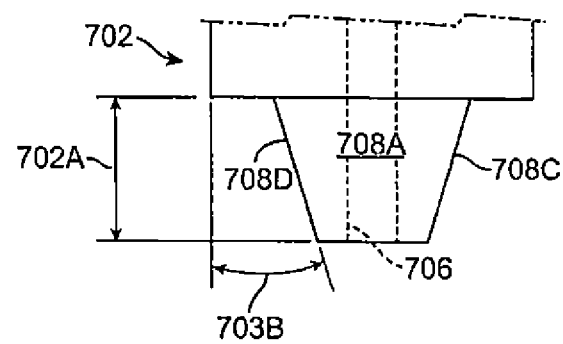
FIG. 16A
FIG. 16B
FIG. 16D
FIG. 16C

METHOD FOR FORMING A COATING ON A STENT

CROSS-REFERENCE TO RELATED APPLICATION

This application is a continuation of application Ser. No. 14/479,080, filed Sep. 5, 2014, now U.S. Pat. No. 9,849,481, which is a continuation of application No. 13/759,001, filed Feb. 4, 2013, now U.S. Pat. No. 8,846,131, which is a divisional of application Ser. No. 12/027,947, filed Feb. 7, 2008, now U.S. Pat. No. 8,367,150, which is a continuation-in-part of application Ser. No. 11/764,006, filed on Jun. 15, 2007, now U.S. Pat. No. 7,897,195, the entire contents of which applications are incorporated by reference for all purposes.

BACKGROUND OF THE INVENTION

Field of the Invention

This invention relates to methods and devices for coating stents.

Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site. Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for scaffholding but also as vehicles for providing biological therapy. Biological therapy uses medicated stents to locally administer a therapeutic substance. To reach effective concentrations at the treated site via systemic drug administration often produces adverse or even toxic side effects. Local delivery is a treatment method because it administers smaller total medication levels than systemic methods and the drug is delivered to a specific site. Local delivery thus produces fewer side effects and achieves better results.

A medicated stent may be fabricated by coating the surface of a stent with an active agent or an active agent and a polymeric carrier. Those of ordinary skill in the art fabricate coatings by applying a polymer, or a blend of polymers, to the stent using well-known techniques. Such a coating composition may include a polymer solution and an active agent dispersed in the solution. The composition may be applied to the stent by immersing the stent in the composition or by spraying the composition onto the stent using various kinds of apparatus. The solvent then evaporates, leaving on the stent surfaces a polymer coating impregnated with the drug or active agent.

The accuracy of drug loading, the uniformity of the drug distribution, stent coating quality, and coating material selection are critical factors in making the drug eluting stent. Having a robust and cost effective drug eluting stent manufacturing process to enable good coating quality, high throughput, high yield, low machine down time is an important goal for coated stent manufacturers.

SUMMARY OF THE INVENTION

Briefly and in general terms, the present invention is directed to a method for forming a coating on a stent.

In aspects of the invention, a method comprises: spraying or drying a coating on the stent while the stent is supported on a mandrel assembly, the stent having a first end, the stent supported such that a first part of the stent at the first end is in contact with the mandrel assembly; and during the spraying and drying, making the first part of the stent go out of contact with the mandrel assembly by vibrating the mandrel assembly.

BRIEF DESCRIPTION OF THE DRAWINGS

FIGS. 14A and 14B depict the stent crowns at a "W" end and a "U" end of the stent of FIG. 12A relative to the portions of the collet of FIG. 11A when the stent is supported on a mandrel assembly according to the second embodiment.

FIGS. 15A and 15B depict the location of stent crowns at a "W" end and a "U" end of the stent of FIG. 13A relative to the collet of FIG. 11A when the stent is supported on a mandrel assembly according to the second embodiment.

FIGS. 16A, 16B, 16C, 16D and 16E depict perspective, frontal and side views of a third embodiment of a collet.

DETAILED DESCRIPTION OF THE INVENTION

Embodiments of the present invention relate to coating implantable medical devices such as stents. In particular, the embodiments of the present invention relate to methods and devices for spray coating and drying stents.

A stent may have virtually any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. Embodiments of the present invention are applicable to virtually any stent design and are, therefore, not limited to any particular stent design or pattern. One embodiment of a stent pattern may include cylindrical rings composed of struts. The cylindrical rings may be connected by connecting struts.

In some embodiments, a stent may be formed from a tube by laser cutting the pattern of struts in the tube. The stent may also be formed by laser cutting a metallic or polymeric sheet, rolling the pattern into the shape of the cylindrical stent, and providing a longitudinal weld to form the stent. Other methods of forming stents are well known and include chemically etching a metallic or polymeric sheet and rolling and then welding it to form the stent.

In other embodiments, a metallic or polymeric filament or wire may also be coiled to form the stent. Filaments of polymer may be extruded or melt spun. These filaments can then be cut, formed into ring elements, welded closed, corrugated to form crowns, and then the crowns welded together by heat or solvent to form the stent.

Figure 1:
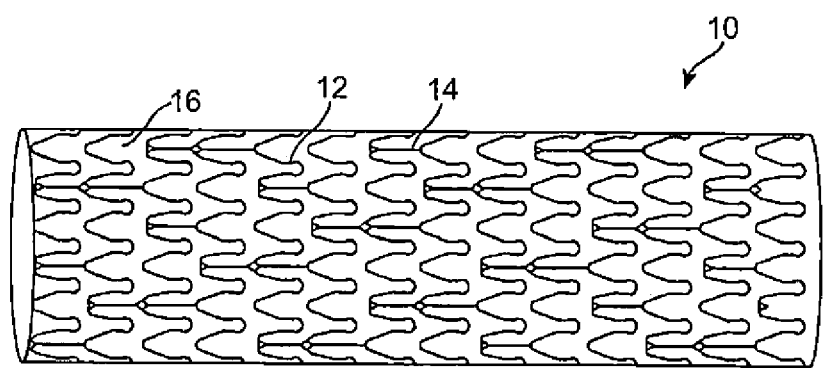
FIG. 1 depicts a side view of a cylindrically-shaped stent.

FIG. 1 illustrates a conventional stent 10 having a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

The cross-section of the struts in stent 10 may be rectangular- or circular- shaped. The cross-section of struts is not limited to these, and therefore, other cross-sectional shapes are applicable with embodiments of the present invention. Furthermore, the pattern should not be limited to what has been illustrated as other stent patterns are easily applicable with embodiments of the present invention.

The surface of an implant (surface energy, composition, roughness, and topography) plays a major role during the initial phases of the biological response (such as protein adsorption, cellular adherence, as well as chronic phases of responses) to the implant. So, having good coating quality of the drug eluting stents (DES) is an important factor in minimizing the biological adverse effect.

Spray coating has been widely used by drug eluting stent (DES) manufactures. The spray process is a relatively simple, fast, and cost effective way of applying coating over the stent. The typical set-up includes a fixturing (mandrel/coil/collet) to hold the stent in place to enable the stent to rotate and translate under a spray nozzle (and a heat nozzle). The coating solution is delivered to the nozzle tip by a metering system and it gets atomized into small droplets by the air or other external supplied forces (ultrasound, electrical). The ideal case is to have a coating process that can produce defect-free DES. But depending on the stent fixture design, it is inevitable that there will be some compromised areas induced by the contacting of the stent to the fixture.

Features of a mandrel design that lead to good coating quality include small contact areas to minimize the contact defect, easy of use, maintaining stent and mandrel 1 to 1 rotation, and clean-ability. A collet having a conical surface exhibits these traits. Collets having less surface area than a cone can also provide desirable features and, in addition, further reduce coating defects and/or enhance coating quality over a conical surface. Moreover, the surfaces may be designed according to the stent geometry to further improve coating quality and reduce defects, as will be understood from the following disclosure.

By removing part of the surface areas on a conical surface, but still maintaining a self centering capability for the stent, a collet can not only still provide a good support to the stent but eliminate the unnecessary contact points of the stent to the mandrel. The stent-collet contact points, e.g., only two or three at each end of the stent, can be precisely moved to the next open peak, crown, edge, etc. by using a mechanism to rotate the collet relative to the stent. Stent contact points during the previous spray cycle are now open for the next spray cycle.

As indicated above, a medicated coating on a stent may be fabricated by spraying a coating composition including polymer and drug on the stent. Spray coating a stent typically involves mounting or disposing a stent on a support, followed by spraying a coating material from a nozzle onto the mounted stent.

A spray apparatus, such as EFD 780S spray device with VALVEMATE 7040 control system (manufactured by EFD Inc., East Providence, R.I.) can be used to apply a composition to a stent. An EFD 780S spray device is an air-assisted external mixing atomizer. The composition is atomized into small droplets by air and uniformly applied to the stent surfaces. Other types of coating applicators, including air-assisted internal mixing atomizers (such as IVEK SonicAir nozzle), ultrasonic applicators (such as Accu-Mist nozzle or MicroMist nozzle from SonoTek Co. in Milton, N.Y.), or a drop dispensing device can be used for the application of the composition.

To facilitate uniform and complete coverage of the stent during the application of the composition, the stent can be rotated about the stent's central longitudinal axis. Rotation of the stent can be from about 1.0 rpm to about 1000 rpm, more narrowly from about 30 rpm to about 200 rpm. By way of example, the stent can rotate at about 150 rpm. The stent can also be moved in a linear direction along the same axis. The stent can be moved at about 1 mm/second to about 30 mm/second, for example about 6 mm/second, or for a minimum of at least two passes (i.e., back and forth past the spray nozzle). In other applications, the spray nozzle can be devised to translate over the stent. The stent is rotated at a desired speed underneath the nozzle.

A nozzle can deposit coating material onto a stent in the form of fine droplets. An atomization pressure of a sprayer can be maintained at a range of about 5 psi to about 30 psi. The droplet size depends on factors such as viscosity of the solution, surface tension of the solvent, solution feed rate, and atomization pressure. The flow rate of the composition from the spray nozzle can be from about 0.1 mg/second to about 10.0 mg/second, for example about 1.0 mg/second. Only a small percentage of the composition that is delivered from the spray nozzle is ultimately deposited on the stent depending on the transfer efficiency of the spray setup. By way of example, when a composition is sprayed to deliver about 1 mg of solids, only about 100 micrograms or about 10% of the solids sprayed will likely be deposited on the stent. The solid percent in the composition typically can range from 0.1 wt % to 15 wt %, for example about 5 wt %.

To reduce or eliminate coating defects in coated stents, excessive solvent in the applied coating material is removed through an in-process drying cycle. Excessive application of the polymer or excessive solvent left in the coating can cause coating defects such as pool web (excessive material accumulated between stent struts) due to the lack of good wettability of the coating droplets over a stent with a tight geometry.

To improve the coating quality, the coating process can involve multiple repetitions or cycles of spraying forming a plurality of layers. A repetition can involve a single pass or multiple passes of moving a spray nozzle (or moving the stent). A pass means moving the nozzle from one end (e.g., proximal end) to the other end (e.g., distal end) of a stent. Each repetition can be, for example, about 0.5 second to about 20 seconds, for example about 10 seconds in duration. The amount of dry coating applied by each repetition can be about 1 microgram/cm$^2$ (of stent surface) to about 75 micrograms/cm$^2$, for example, less than about 20 micrograms/cm$^2$.

As indicated above, the coating composition can include a polymer and a drug dissolved in a solvent. Each repetition can be followed by in-process drying involving removal of a significant amount of the solvent(s). In an embodiment, there may be less than 5%, 3%, or more narrowly, less than 1% of solvent remaining in the coating after in-process drying between repetitions. When the coating process is completed, all or substantially all of the solvent may be removed from the coating material on the stent. Any suitable number of repetitions of applying the composition followed by removing the solvent(s) can be performed to form a coating of a desired thickness or weight. Excessive application of the coating material can, however, cause coating defects.

Embodiments of the present invention may be illustrated by reference to the exemplary spray coating device 200 depicted in FIGS. 2, 3, 4 and 5 which is described in greater detail in U.S. application Ser. No. 11/764,006, herein incorporated by reference in its entirety for all purposes. Device 200 is configured to process two stents simultaneously. However, device 200 can process only one stent if desired. Device 200 has a spraying zone 202 and a drying zone 204, which enable coating of one stent and drying of another stent simultaneously. Stent support assemblies, mandrels 208 and 222 can be moved between spraying zone 202 and drying zone 204 via a rotating drum to allow simultaneous spraying of a stent on one stent support assembly and drying of another stent on another stent support assembly.

Spraying zone 202 has a spray nozzle 206 that is mounted above movable stent support assembly 208. As depicted by an arrow 242, stent support assembly 208 is rotated during the coating process. Spray nozzle 206 is translatable along a y-direction, as shown by double-headed arrow 205, along the axis of stent support assembly 208. Spray nozzle 206 is also movable along an x-direction as shown by an arrow 207.

Spray nozzle 206 is dwelled in a nozzle holder 220 which is attached to a mounting bracket block 218. Mounting bracket block 218 is coupled to a linear slide that can control movement of nozzle holder 220 and spray nozzle 206 back and forth in the x-direction during the application of the coating material over the stent. Mounting bracket block 218 is also coupled to a sliding stage to enable nozzle holder 220 along with spray nozzle 206 to side shift back and forth in the x-direction (245/207) to a position over upper funnel 214A after a spray cycle is complete. The side-shifting of nozzle holder 220 along with spray nozzle 206 clears the path in the spray zone to allow the drum 240 to rotate to advance the stent at the drying zone 204 to the spraying zone 202 to receive coating material.

Drying zone 204 includes a drying nozzle 224 that can be positioned over a movable mandrel assembly 222 for supporting a coated stent during drying. Mandrel assembly 222 is inserted into a spindle 228, which rotates the mandrel assembly 222 during the drying process, as indicated by an arrow 243. In some embodiments, the same motor may provide rotational motion to stent support assemblies 208 and 222. Drying nozzle 224 includes an electrical heater 230 to generate heated gas for drying nozzle 224. Drying nozzle 224 is movable and can shift in an x-direction, as shown by a double-headed arrow 245, from its position shown in FIG. 2 to a drying position over mandrel assembly 222. Drying nozzle 224 can be positioned above mandrel assembly 222 so that it can dry a stent coated in spraying zone 202 by blowing warm gas over a freshly coated stent. Stent grippers 250 and 252 for clocking a stent, as described in detail below, are disposed below mandrel assembly 222. Heater 230 is movable in the x-direction as indicated by 502 (see FIG. 4A).

Side shifting of drying nozzle 224 and spray nozzle 206 may be accomplished with pneumatic slides or motor driven linear slides. This side-shift allows the indexing drum to rotate, and can also accommodate differences in the drying time and the spraying time. The side-shift of drying nozzle 224 to a deflection plate 508 of the drying air away from the stent to prevent over-drying while the other stent is finishing its spray cycle.

Stent support assemblies 208 and 222 are supported at their distal ends by clamps 226 and 227, respectively. The proximal end of mandrel assembly 222 is shown supported by a spindle 228 in both the spray and dry zones. The proximal end of stent support assembly 208 is supported in the same manner, but is hidden by spray nozzle 206. The spindle 228 is mounted or coupled on a drum 240 which rotates as shown by arrow 232. Rotatable drum 240 can rotate to reverse the position of stent support assemblies 208 and 222 so that stent support assembly 208 is in drying zone 204 and mandrel assembly 222 is in the spray zone 202.

Figure 5A:
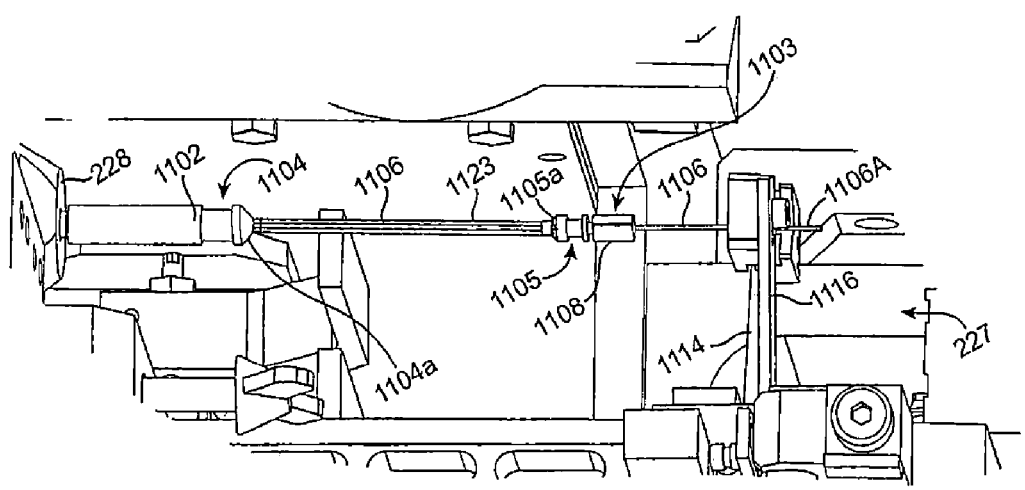
FIGS. 5A, 5B and 5C depict perspective views of a drying portion of the device of FIG. 2, including a mandrel assembly, spindle and support bracket for the mandrel assembly.
Figure 5B:
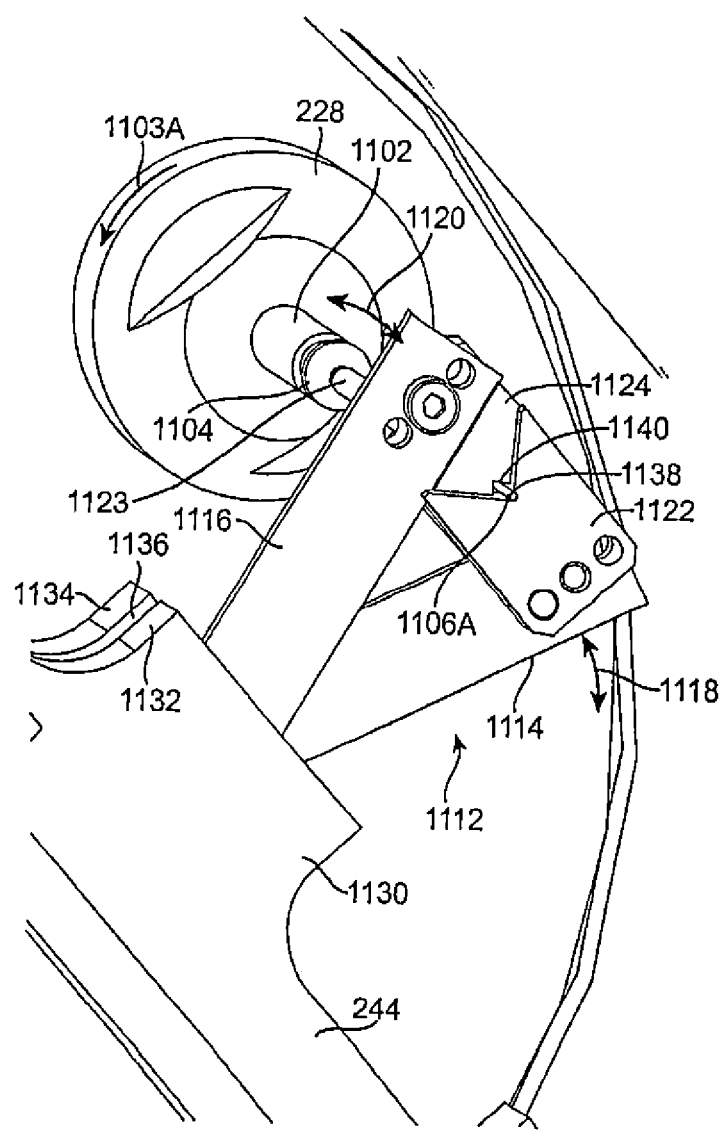
Figure 5C:
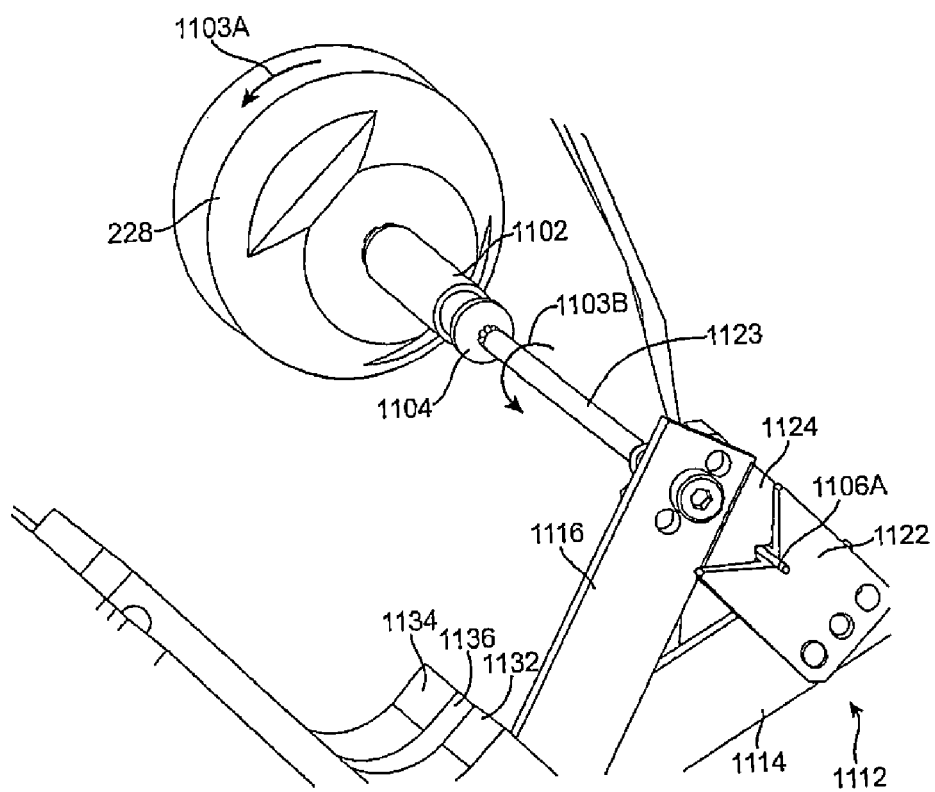

Referring to FIGS. 5A-5C, the jaw-like end support 227 provides alignment, support and facilitates automatic loading/unloading of a mandrel and stent on the spindle 228. For example, a mandrel assembly 222 having a finished stent 1123 mounted thereon can be removed from the device 200 by opening the jaws 1122, 1124 associated with support 227 (FIG. 5B), then de-coupling collet 1104 from shank 1102. A new mandrel or support assembly 222 with stent is then placed in the device 200 by coupling a proximal collet 1104 to shank 1102, placing pin end 1106 on lower jaw 1122, and then closing the jaws 1122 and 1124.

Referring again to FIG. 2, device 200 is designed to allow spraying of stent in spray zone 202 while a coating layer previously applied at spray zone 202 is dried at drying zone 204. Simultaneous spraying and drying reduces or eliminates idle time of sequential spraying and drying operation, thus increasing the throughput of a coating operation.

Specifically, a layer of coating material is applied to a first stent mounted on stent support assembly 208 by spray nozzle 206. At the same time, a second stent mounted on mandrel assembly 222 with coating material already applied in spray zone 202 is dried by drying nozzle 224. When both the spray coating on the first stent and drying of the second stent are completed, rotatable drum 240 rotates and positions the second stent (dried) at spray zone 202 and the first stent (freshly coated) at drying zone 204. The first stent may then be dried at drying zone 204 and a layer of coating material can be applied to the second stent at spray zone 202. The spraying and drying can be repeated a selected number of times as necessary to obtain a desired coating mass on each of the stents. Rotatable drum 240 can rotate clockwise or counterclockwise to change the position of the first stent and second stent between spray zone 202 and drying zone 204. Stent support assembly 208 and stent mandrel assembly 222 are rotated in each spraying and drying cycle. As shown by arrow 232, the first stent is rotated to spray zone 202 and the second stent is rotated to drying zone 204, and after the spraying/drying cycle is complete the first stent is rotated back to drying zone 204 for drying the stent and the second stent is rotated to spray zone 202 to receive coating material.

Figure 4A:
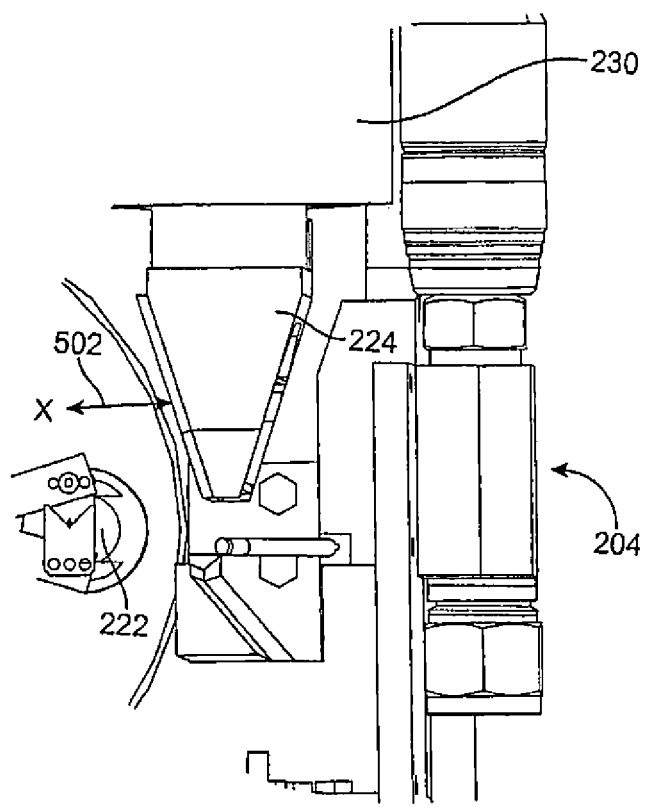
FIGS. 4A and 4B depict perspective views of a drying portion of the spray device of FIG. 2.
Figure 4B:
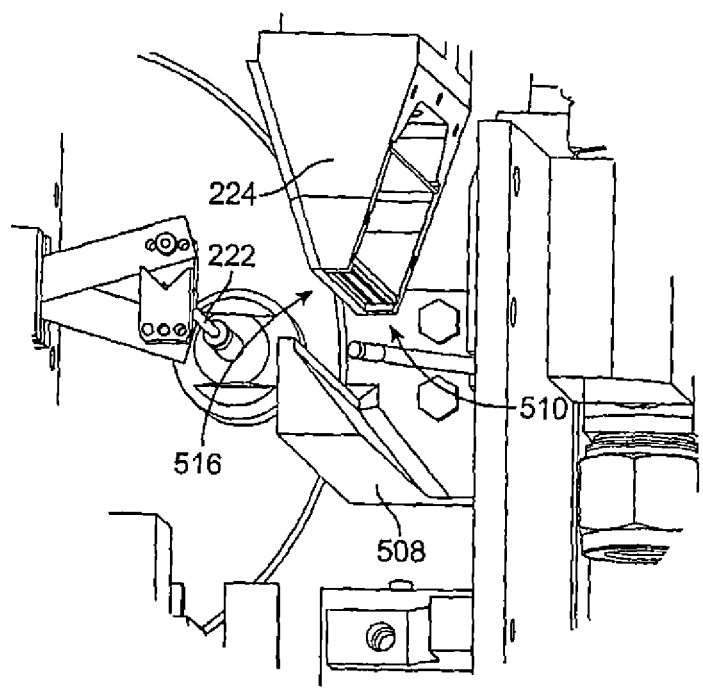

FIG. 4B shows a slotted opening 510 through which warm gas passes for drying a coated stent mounted on stent support mandrel 222. A deflector shield 508 is positioned below drying nozzle 224 in its right-most shifted position. Deflector shield 508 deflects the warm gas stream exiting drying nozzle 224 to the downstream evacuation when drying nozzle 224 is shifted away from mandrel assembly 222 when the drying cycle is complete. Perforated plates or screens 516 can be incorporated into drying nozzle 224 to improve the mixing of the hot gas exiting from the heating element (not shown) located at the upper portion of drying nozzle 224 to provide an air stream with a uniform temperature distribution.

FIGS. 5A-C depict perspective views of a mandrel assembly 222 for supporting a stent 1123, the supporting equipment for rotating the mandrel assembly 222, and removing/replacing mandrel assemblies in device 200. Collet 1104 is coupled at one end to a shank 1102, which is connected in rotation to spindle or end cap 228. Spindle 228 is adapted for communicating rotational motion through shank 1102 to mandrel assembly 222. The rotation imparted to mandrel assembly 222 through spindle 228 is depicted in FIG. 5B by an arrow 1103A, and the double arrow in FIG. 6 (rotation axis "A"). This rotational motion occurs during the stent spraying and/or drying process and may also occur between spraying and drying cycles to reduce coating defects on the stent, as discussed below.

Referring to FIG. 5B, an end 1106A of the mandrel assembly pin 1106 is held by a tailstock support 1112 during spraying and drying. Tailstock support 1112 is a jaw-like mechanism with two movable flat extension arms 1114 and 1116 that can open as shown by arrows 1118 and 1120, respectively. Flat extension arms 1122 and 1124 with opposing wedge- or v-shaped cut-out sections are coupled to ends of movable arms 1114 and 1116. Support fixture 1130 is composed of two end plates 1132 (outer) and 1134 (inner) that are used to house and support flat extension arms 1114 and 1116. Proximal ends of extension arms 1114 and 1116 are connected to two bars (one at an upper location and one at a lower location) which are linked to an air cylinder to pull them up or down to close or open the tailstock support. End 1106A of pin 1106 is held between jaws 1138 and 1140 formed by opposing wedge-shaped cut-out sections of plates 1122 and 1124. In this action, end 1106a may be adequately supported to prevent excessive run-out when spindle 228 is rotated. Further, this mechanism permits the stent 1123 to be easily dismounted by separating jaws 1138 and 1140 and decoupling the stent supporting assembly 222 from the shank 1102. A finished stent 1123 and mandrel assembly 222 can then be removed from the device 200.

As mentioned earlier, it is desirable to reduce or perhaps eliminate coating defects that can result from stent contact with supports, such as mandrels, during coating. While some coating defects can be minimized by adjusting the coating parameters, other defects occur due to the nature of the interface between the stent and the apparatus on which the stent is supported during the coating process. Surface contact between the stent and the supporting apparatus can create regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the needed coating from the stent and leaving bare areas. Alternatively, the excess coating may stick to the stent, thereby leaving excess coating as clumps or pools on the struts or webbing between the struts. Thus, it is desirable to minimize the influence of the interface between the stent and the supporting apparatus during the coating process to reduce or eliminate coating defects.

Coating defects associated with the stent-mandrel contact points can be minimized by addressing the manner in which the stent is mounted to a mandrel, the design of the mandrel collets and the manipulation of the stent and/or mandrel between the coating and drying cycles discussed earlier. These methods and apparatus will now be discussed in greater detail by reference to embodiments of mandrel assembly 222.

Figure 6:
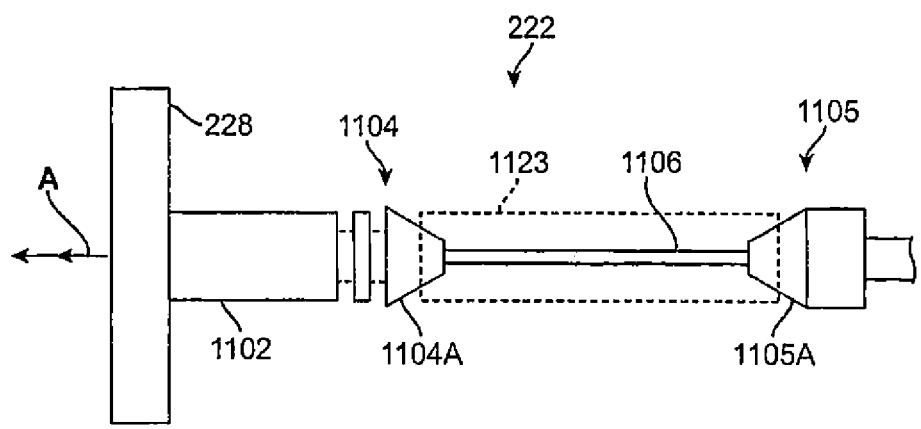
FIG. 6 depicts a side view of the mandrel assembly in FIGS. 5A-5C, which has collets according to a first embodiment.

Mandrel assembly 222 according to one embodiment is shown in side view in FIG. 6. Proximal collet 1104 and distal collet 1105 have conical-like, or tapered cylinder surfaces 1104A and 1105A, respectively, which support proximal and distal ends of the stent 1123 on mandrel assembly 222. Stent 1123 is supported by collets 1104 and 1105 such that at least a portion of the surface 1104A and 1105A is received within the bore of the stent 1123. Collets 1104, 1105 are connected through a pin 1106 which can be slidingly received through a bore formed in collet 1105 and fixed at one of its ends to collet 1104. The pin 1106 has a diameter less than the stent 1123. For example, the pin 1106 has a diameter between about 0.010" and 0.030". Pin 1106 can be made of a metallic material such as Nitonol wire or other suitable material that provides adequate bending and torsional stiffness properties.

As implied above, collets 1104, 1105, pin 1106 and the stent 1123 are pre-assembled before being placed into device 200.

Collet surfaces 1104A and 1105A can have a roughened surface to absorb excess coating material, which can reduce coating defects. For example, a micro-blasting tool can be applied to the surfaces 1104A, 1105A to create a micro depot surface to help spread out, or channel away overspray. The finish of the surface can be controlled by the type of bead, duration of treatment, and pressure of the air supplied.

In some embodiments, stent 1123 is gently pinched between collets 1104, 1105 and in other embodiments a predetermined gap, or lose contact is made between the stent and collets when the mandrel assembly 222 is assembled. In some embodiments a gap or lose contact will reduce coating defects by a significant amount. When a stent is pinched between collets, the surface-to-surface contact between the stent and the collets is greater then when a lose contact is made. In addition, surfaces are brought closer together. Hence, with increased surface contact and surfaces brought closer together, the coating material will have more of a tendency to buildup between or near the surfaces due to wicking, thereby leading to undesirable webbing or bridges formed over the stent, or even bare spots on the stent surface.

During assembly, a gap or lose fit may be achieved as follows. First, collet 1104 with pin 1106 is placed vertical and stent 1123 dropped down over pin 1106 so that it rests on collet surface 1104A. The distal collet 1105 is then inserted onto pin 1106 and moved down until the collet 1105 is barely touching the distal end of the stent 1123. This gap may be a few thousands of an inch. Further, it has been found that when there is only a lose contact between the stent 1123 and mandrel assembly 222, as opposed to pinching the stent between the collets 1104, 1105, the mandrel assembly still achieves a one-to-one ("1:1") rotation between the stent 1123 and the collets 1104, 1105. That is, there is no slippage of the stent on the mandrel assembly 222 during spraying and drying cycles. Further, with this lose fitting, the stent 1123 can still be properly aligned so that the stent 1123 will not touch the pin 1106 to minimize any stent inner diameter defects.

In some embodiments, a stent may be periodically separated from the collet surfaces during a spraying or coating cycle as the mandrel assembly 222 rotates. With the stent 1123 periodically separated from the collets, there can be less buildup of material and, therefore, a reduction in coating defects. In some embodiments, an ultrasonic vibration is periodically supplied to the pin 1106, resulting in a vibration of the collets which can break any adhesion between the stent 1123 and collet 1104, 1105 contact points caused by the sprayed coating material. The same break-up may be achieved by periodically supplying a pulse or puff of air to the stent, thereby temporarily dislodging the stent from the collet surfaces. In some embodiments, the stent is loaded onto the collets 1104, 1105 such that the stent longitudinal axis is offset from the rotation axis A of the mandrel assembly 222 (FIG. 6). In these embodiments, the stent 1123 will separate from collets (displacing laterally of axis A) as the mandrel assembly 222 rotates due to the offset between the stent axis and axis A. This can also help to reduce any stent inner diameter defects.

Figure 2:
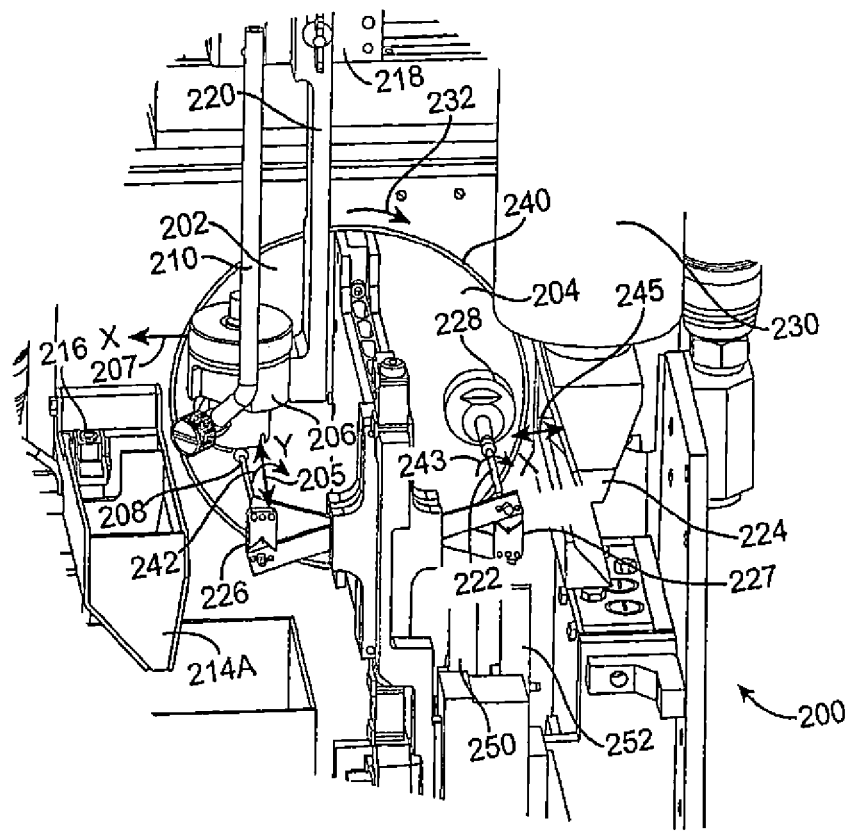
FIG. 2 depicts a perspective view of a device used to coat stents.
Figure 3:
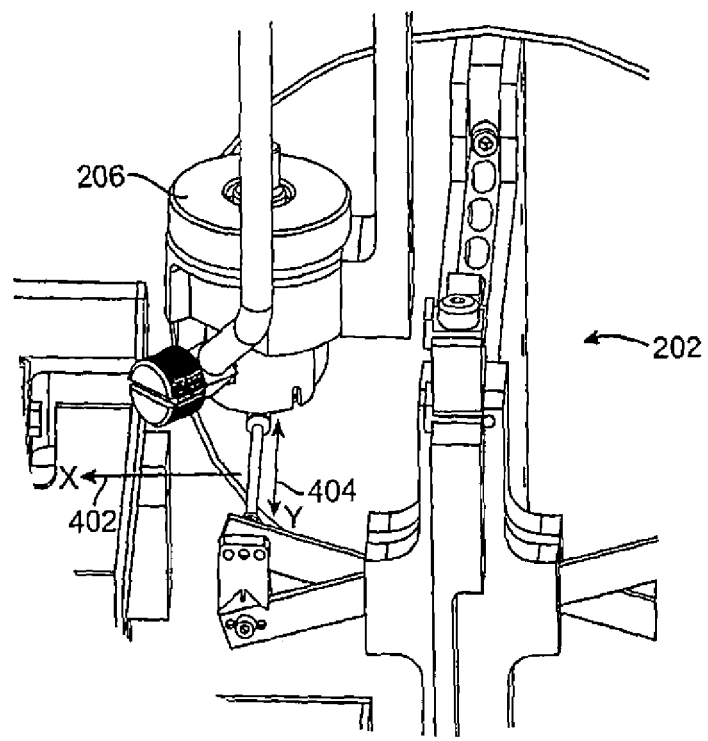
FIG. 3 depicts a perspective view of a spraying portion of the device of FIG. 2.
Figure 7A:
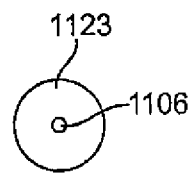
FIGS. 7A, 7B and 7C depicts a mechanism for restraining stent rotation between spray cycles.
Figure 7A:
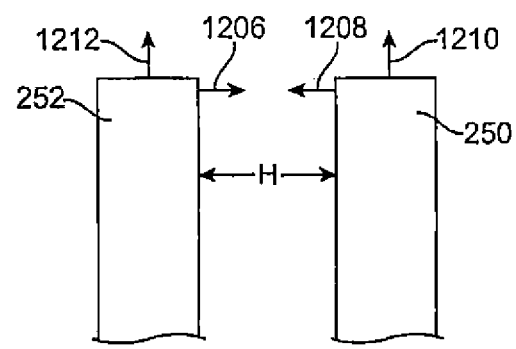

In some embodiments the stent is restrained and the collets shifted back and forth (i.e., brief clockwise, followed by counterclockwise rotations) to break-up any adhesion between the stent and the collets. This process may be performed between each spraying and drying cycle. For example, this process may be performed when the mandrel assembly 222 is positioned in the drying zone 204 and just following a drying cycle. The rotational motion may be supplied by the spindle 228. As shown in FIG. 2 and in FIGS. 7A-7C, stent gripper plates 250 and 252 provide a mechanism to steadily hold the stent while the mandrel assembly 222 is rotated so as to change or shift contact points between the stent and the collets, or simply to break-up any adhesion between the stent and the collets. FIG. 7A depicts a close-up view of stent gripper plates 250 and 252 from FIG. 2, which are positioned below the stent mandrel assembly 222 (as depicted by stent 1123 and pin 1106). Stent gripper plates 250 and 252 are disposed at a distance H from one another initially, the distance H being greater than the outside diameter of a stent that is being coated. Plates 250 and 252 can be shifted toward each other as shown by arrows 1206 and 1208 and upwards 1210, 1212 towards the stent 1123 between spraying cycles.

Figure 7B:
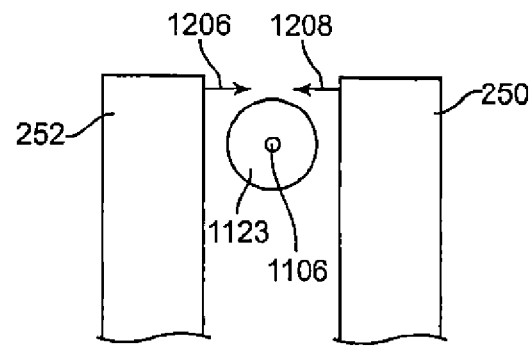
Figure 7C:
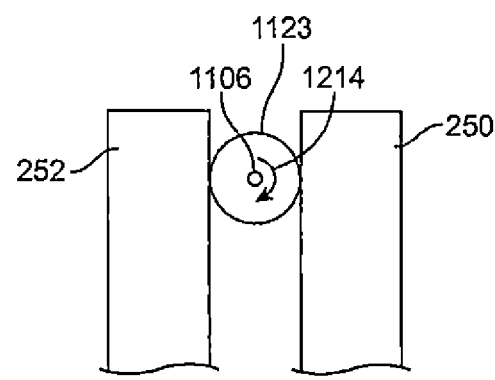

Upon drying of a stent, stent gripper plates 250 and 252 are first shifted upwards towards the mandrel assembly 222 so that stent 1123 is between plates 250 and 252, as depicted in FIG. 7B. Stent gripper plates 250 and 252 then move towards one another as shown by arrows 1206 and 1208. As depicted in FIG. 7C, stent grippers 250 and 252 move close to each other to form a predetermined gap suited to gently hold stent 1123 while mandrel assembly 222 is rotated relative to stent 1123, as represented by arrow 1214 in FIG. 7C. The mandrel assembly 222 can be rotated or clocked just enough to move any contact points between stent 1123 and any part of the mandrel assembly, for example, less than 5°. Alternatively, the mandrel assembly 222 can be rotated greater than 5°, 10°, 30°, 60°, 90°, 270°, or greater than 360° between each or some of the spraying cycles. In addition, the mandrel assembly can be rotated clockwise or counterclockwise. The rotating or clocking can be uni-directional or bi-directional. For example, the mandrel assembly can be clocked back and forth one or more times.

Figure 8A:
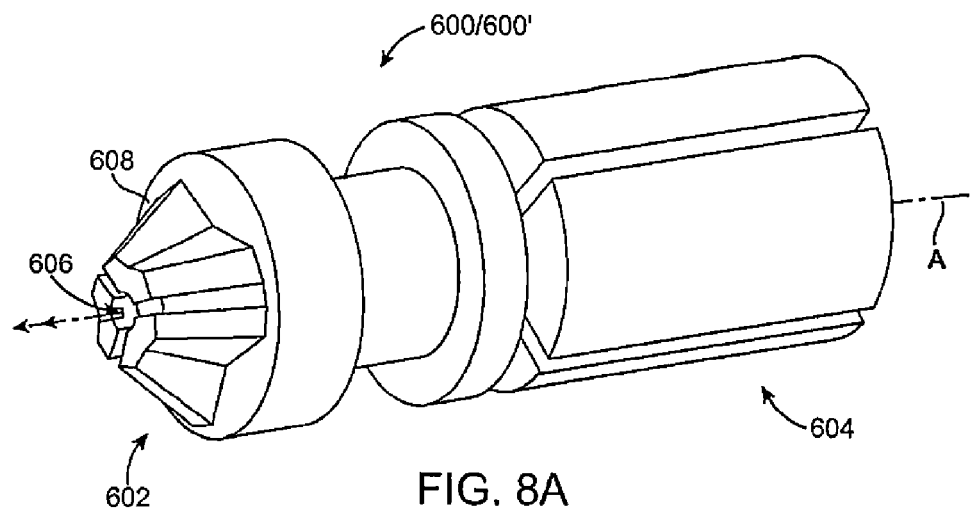
FIGS. 8A and 8B depict features of a second embodiment of collets for the stent mandrel assembly of FIG. 6.

In some embodiments the mandrel assembly 222 may have collets with collet surfaces that take a form intended to place less of the stent in contact with the collet, that is, less than the surface contact between a stent and a tapered cylinder or truncated cone as in the case of collets 1104 and 1105. FIG. 8A depicts a perspective view of a collet 600 according to embodiments that include a stent contacting end 602, which has stent-contacting surfaces 608 distributed over, or lying within an imaginary surface, such as a truncated cone, or tapered cylinder imaginary surface. Collet surfaces 608 contact less of the stent than collet surface 1105A. In one sense, collet 600 may be viewed as a collet with conical surfaces 608 but with portions of the cone removed so that surfaces 608 have only a portion of surfaces 1104A and 1105A to contact the stent. As such collet 600 may be formed from a collet 1104 with grooves, notches or depressions formed on the stent-contacting surface 1104A.

Collet 600 includes an end 604 that may be used to grip collet 600 by a tool, such as a tool used to place collet 600 over the pin 1106, or remove the collet 600 from the pin 1106. A bore having an opening 606 for receiving or withdrawing the pin 1106 from the collet 600 when a stent is mounted on, or dismounted from the pin 1106 is provided at the geometric center, or axis of rotation A of the mandrel assembly 222. In the following discussion, collet 600 shares the same properties as, and may be used in device 200 in the same manner as collet 1105 except where the following discussion makes apparent the distinctions between collet 1105 and collet 600. Collet 600 may be used at both the proximal end (collet 600) and distal end (collet 600') of the mandrel assembly 222. Unless otherwise specified, it will be understood that the features discussed earlier in connection with device 200 apply equally to a device that uses collets 600 and 600' in place of collets 1104 and 1105.

Figure 10:
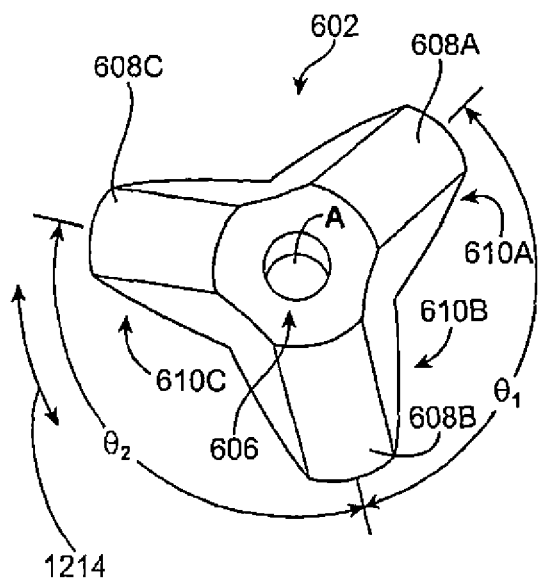
FIG. 10 depicts a frontal view of a stent supporting end of a collet according to the second embodiment.

FIGS. 10 and 11 depict two embodiments of the stent supporting end 602 of collet 600. For convenience, in the following discussion a description of collet support 602 is sometimes made with respect to cylindrical-type coordinates (R, θ, Z) with center at rotation center A. Thus, the axis A is the "Z" axis. End 602 may have three portions 610A, 610B and 610C, each of which providing a surface 608A, 608B, 608C, respectively, intended to contact the stent such that at least a portion of the supporting end 602 is disposed within the stent bore when the stent is supported by collet 600. Portions 610A, 610B and 610C may extend radially outward from hole 606 to provide surfaces 608. Each surface 608 may be rectangular with rounded edges and is placed in contact with one or more crowns or peaks of a stent.

In some embodiments members 610A and 610B are angularly spaced by an angle θ1, and members 610B and 610C by an angle θ2. In some embodiments, the angles θ1 and θ2 may be considered separation angles between surfaces 608. In some embodiments, members 610 may be equally spaced, such as by an angle 120° between each of the three members. In some embodiments there are more than three members 610, in other embodiments less, such as in the case of collet end 702 shown in FIGS. 16A-D.

Figure 8B:
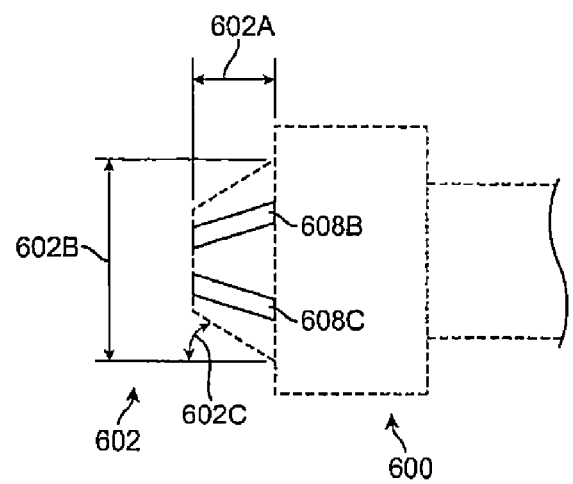
Figure 11A:
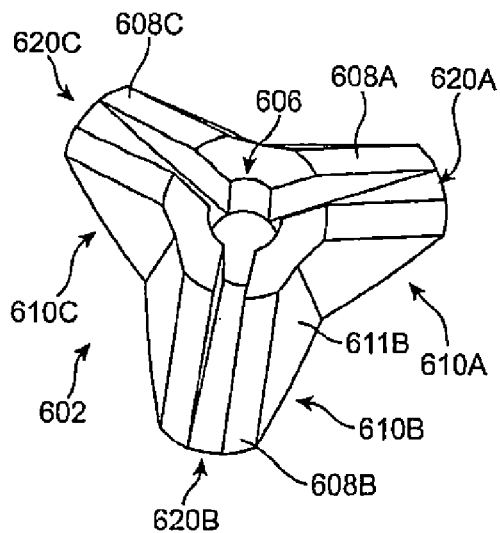
FIGS. 11A and 11B depict the frontal view of FIG. 10 with the stent supporting end having channels formed thereon, and a detailed view of a portion of the stent supporting end.
Figure 11B:
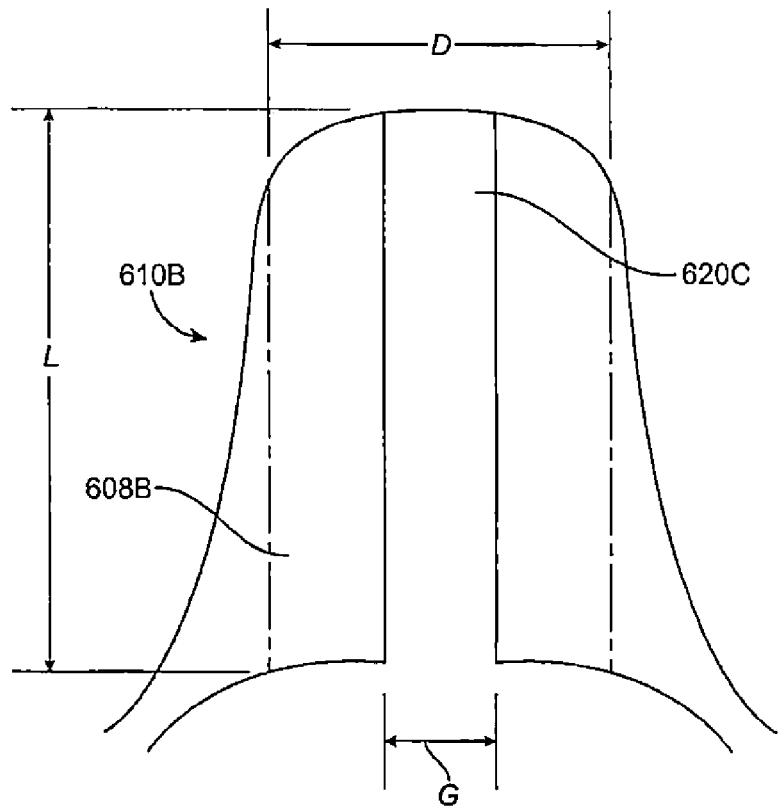

In some embodiments, each member 610 may include a groove, depression, channel or notch 620 extending radially outward from hole 606, as illustrated in FIG. 11A-B. The channels 620A, 620B and 620C bisect each of the respective surfaces 608A, 608B, 608C so that the amount of surface area in contact with the stent is reduced, but with retaining a 1:1 rotation ability during a spray and dry cycle. As mentioned above, surfaces 608 may lie within an imaginary tapered cylindrical or conical surface. Imaginary surface is intended to mean the geometric surface common to all surfaces 608. Thus, with respect to the embodiments of FIGS. 10, 11 the surfaces 608 may be described as lying on the outer surface of a tapered cylinder having a height 602A, outer radius 602B and taper angle 602C, as depicted in FIG. 8B. In some embodiments, the imaginary surface may be an ellipsoid, such as that described by an ellipse "E", as illustrated in FIGS. 16A-16E. Surfaces 608A, 608B, 608C cover less than the entire tapered cylinder, or these surfaces are the portions of the conical surfaces 1104A, 1105A not removed from the collets 1104, 1105. Surfaces 1104A and 1105A of Collets 1104, 1105 cover the entire tapered cylinder.

Figure 12A:
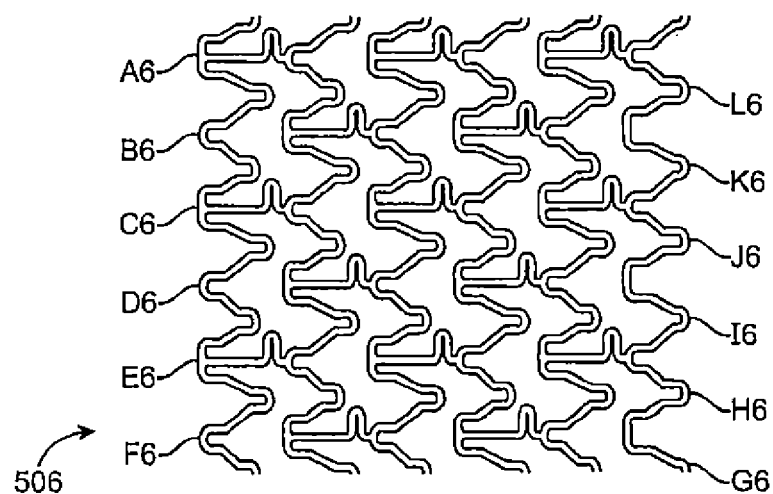
FIGS. 12A, 12B and 12C show a planer and perspective views for a first stent type.
Figure 12B:
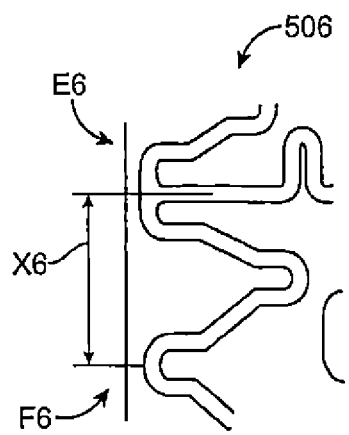
Figure 12C:
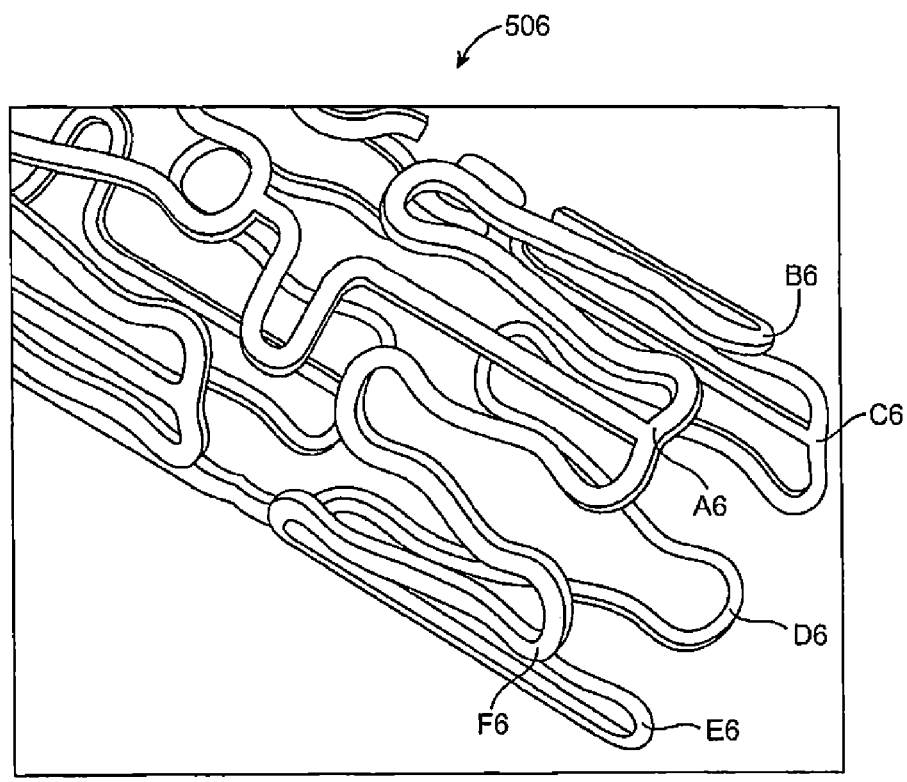
Figure 13A:
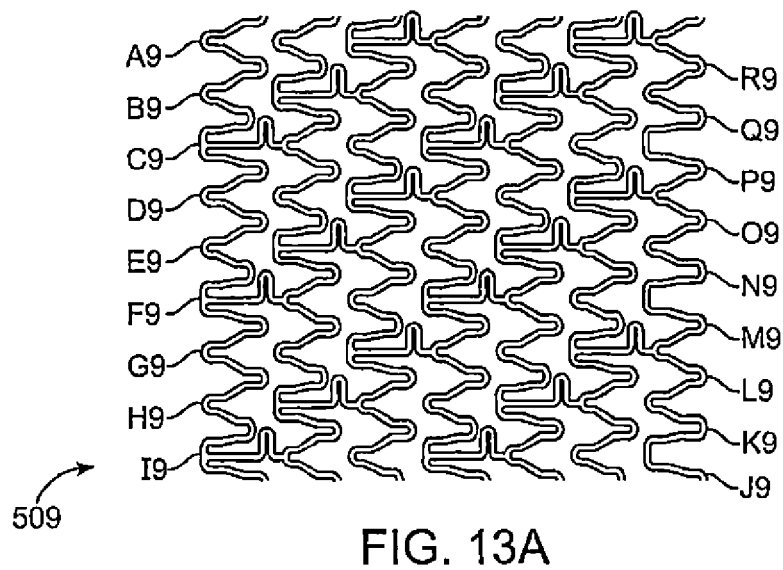
FIGS. 13A and 13B show a planer view, and a portion of the planer view for a second stent type.
Figure 13B:
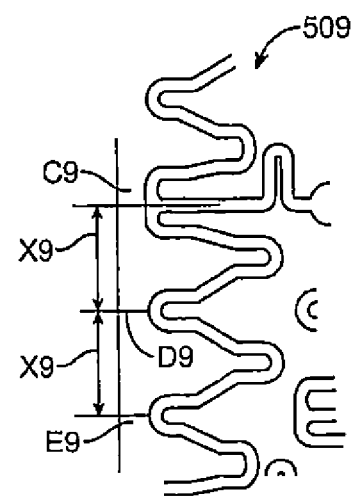

Collets 600 and 600' (see FIG. 8A) may be used to support stents having a repeating pattern of crowns, peaks or bends associated with a proximal/distal end cylindrical segments of the stent. The peaks, crowns or bends may be formed by member(s) forming a sinusoidal, undulating, curvilinear etc. patterns at proximal and distal ends, i.e., those ends that would come into contact with collet surfaces 608. Two such stents, 506 and 509, are shown in plane view in FIGS. 12A and 13A, and a portion of those stents are shown in FIGS. 12B and 13B. The stent 506 illustrated in FIGS. 12A and 12B has six crowns A6 through F6 at a "W" end and six crowns L6 through G6 at a "U" end. Crowns A6 through F6 are also shown in the perspective view of FIG. 12C. The stent 509 illustrated in FIGS. 13A and 13B has nine crowns A9 through I9 at a "W" end and nine crowns J9 through R9 at a "U" end. FIGS. 14A and 14B show the contact points between surfaces 608 and crowns of stent 506 at the distal end (FIG. 14A) and proximal end (FIG. 14B) when stent 506 is supported by collets 600 and 600' as shown in FIG. 8B. Thus, as illustrated in FIGS. 14A-B, crowns F6, B6, D6 of the stent 506 are placed in contact with surfaces 608B, 608C and 608A, respectively; and crowns L6, J6, H6 of the stent 506 are placed in contact with surfaces 608B, 608A and 608C, respectively. Similarly, FIGS. 15A-B depict the contact between collet 600 and crowns of the stent 509. When stent 509 is supported by collets 600 and 600' (FIG. 8B), surface 608B is in contact with crowns A9 and B9, surface 608A is in contact with crowns D9 and E9, and surface 608C is in contact with crowns H9 and G9. At the stent 509 "U" end, surface 608B is in contact with crown K9, surface 608A is in contact with crown Q9, and surface 608C is in contact with crowns N9.

In some embodiments, a stent mounted on collets 600 and 600' may be periodically held while collets 600, 600' rotate so that the contact points between the stent and surfaces 608 are changed. Similar embodiments were discussed earlier in connection with the collets 1104 and 1105. Following a drying or spraying step, the stent may be at least partially restrained in rotation, e.g., using grippers 252, 250, so as to cause a sufficient degree of slippage to occur between collets 600, 600' and stent surfaces when spindle 228 applies a rotation to mandrel assembly 222. This allows contact points to change during the coating process, which can reduce coating defects. Since stent surfaces in contact, or near collet surfaces will be free of the collet in a subsequent spray cycle, buildup of coating material, which causes defects, is minimized or effectively avoided because every surface is sprayed at least once when free of the collet surface.

As the stent 506 or 509 is held and the supporting collets 600, 600' rotated in the direction 1214 (see FIG. 10), surfaces 608 may be moved from a first crown to a second, angularly adjacent crown, a first crown to a third crown, a first crown to a fourth crown, etc. after each coating is applied. In some embodiments, a collet is rotated only a fraction of a crown width between coating cycles, e.g., so that the collet is rotated through a small angle between coating cycles. In some embodiments, the collet may be rotated, 5, 10, 30, 50, 60, 180, 270, or 120 degrees following a spray and coat cycle. For example, in FIGS. 14A-B stent 506 is mounted on collets 600, 600' such that surfaces 608 are placed in contact with the "W" and "U" ends crowns as explained earlier. Collets 600 and 600' are then rotated (clockwise and counterclockwise, respectively) 60 degrees so that surfaces 608B, 608A and 608C are removed from the "u"-shape crowns F6, D6, B6 and placed in contact with the "w"-shape crowns E6, C6 and A6. Simultaneously, the surfaces 608B, 608A, 608C are moved from crowns L6, J6, and H6 to crowns K6, I6 and G6 in FIG. 14B. Alternatively, collets 600, 600' may be rotated only 30 degrees between coatings, such that a crown is centered over a member 610 during one spray cycle, partially over the member 610 in the next spray cycle, and then free of the member 610 for the third spray cycle.

Referring to FIG. 11B, the surfaces 608, e.g., surface 608B, has a width D, a height L and a channel width G. In some embodiments, the dimensions of D and G may be selected based on a particular stent geometry, such as the geometry of stent 506 and/or stent 509. In some embodiments, the surfaces 608 and channels 620 have angular extents, i.e., D and G, that provide a minimum amount of supporting surface area needed to provide 1:1 rotation and self-alignment of the stent, but without causing crowns, peaks, edges, etc. of the stent to stick or get caught within a channel 620 or between successive surfaces 608 as the collet 600 rotates relative to the stent.

As the stent is held and the collets rotate, it is preferred to avoid any sudden changes in the surface-to-surface contact.

For example, if the angle between successive crowns or peaks of the stent is greater then the width D, then the stent may become caught on collet 600 as collet rotates because one or more members 610 becomes trapped between successive peaks or crowns in the stent. This may damage the stent. Similarly, if the width G of the channel 620 is about the width of, or larger than a crown or peak, then the crown or peak of the stent may become trapped within the channel 620 as the collet is rotated to a new position under the stent. Again, this can damage the stent. In one embodiment, D is selected so that it is at least equal to the length X6 in FIG. 12B, or at least twice the length of X9 in FIG. 13B. In some embodiments, G is selected so that it is smaller than the width of a peak or crown. This should avoid a tendency for the stent crowns to fall or key into a channel or between successive members when the collet is rotated relative to the stent. In some embodiments a gap is formed between the stent collets, as discussed earlier, rather than pinching the stent between collets as this may further reduce instances of the stent becoming caught between successive surfaces 608, or at least enabling stent crowns to safely ride over changes in the collet surface without damage to the stent. The ability for the stent crowns to negotiate over changes in the collet surface may be improved by forming gradual changes in the collet surface. For example, the slopes 611B may gradually transition to surfaces 608 rather than abruptly, as in the case of a right angle, so that crowns of the stent will have less tendency to get caught on a corner of the collet supporting end 602 when the collet 600 is rotated.

Figure 16E:
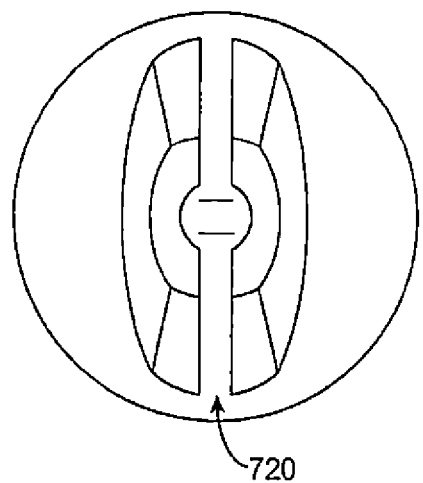

Referring to FIGS. 16A-16E, in a third embodiment a collet 700 has a stent supporting end 702 with a pair of opposing surfaces 708A, 708B that lie within an imaginary elliptical surface based on an ellipse E. A collet 700 may be used for both proximal and distal collets of the mandrel assembly 222 and may function in the same manner as earlier embodiments. According to the third embodiment, less surface area is used to support the stent. In contrast to the embodiments shown in FIGS. 10, 11, the stent supporting end 702 has only two stent-contacting surfaces 708A, 708B which are spaced about 180° from each other, as shown in FIG. 16D. Surfaces 708C, 708D, which extend essentially over a length equal to the major axis of the ellipse, are formed as curved surfaces that lie inside the surface of the ellipsoid. Side surfaces 708C and 708D have a taper angle 703B that is less than the taper angle 703A for the surfaces 708A and 708B that lie on the ellipsoid. For example, taper 703B may be 10 degrees and taper 703A may be 30 degrees. Collet end 702 may also include rounded edges 709 so that stent crowns can pass over the corners when the collet 700 is rotated. In some embodiments, stent supporting end 702 further includes a notch 720 as shown in FIG. 16E. Like notches or channels described in connection with collets 600 and 600', further reduces surface area contact while also adequately supporting and self-centering stent when it is loaded on mandrel assembly 222. With regards to collet 700, it is preferred that a gap or lose fit is made between the stent, e.g., stent 506 or 509, and the collets 700, 700', rather than pinching the stent between the collets. This will ensure that collet 700 can be rotated relative to the stent between spray and dry cycles without causing damage to the stent. This type of fit will also reduce buildup of coating material, as discussed earlier.

Collet 700 may be rotated through different angles when the collet 700 is repositioned with respect to the stent. For example, with reference again to FIG. 14A, and replacing collet 600 with collet 700, surface 708A is in contact with "u"-shape crown F6 and surface 708B is in contact with "w"-shape crown C6. After a drying or spraying step is complete, the stent 506 may be held in rotation and collet 700 rotated through an angle of 60° or 120° so as to remove surfaces from crowns C6 and F6 to crowns B6 and F6, or D6 and A6, respectively, when collet is rotated counterclockwise in FIG. 15A. In some embodiments collet 700 may be rotated through a range of angles, in increments of 5, 10, 20, 30, 40, 60, 90 or more degrees as discussed earlier in connection with collet 600.

Collets 600 or 700 can be made of metallic or polymeric (like UHMWPE, Fluorinated polymers like Teflon, PEEK, etc) materials. They could also be injection molded or machined. Metallic material may be preferred to provide rigidity and machine-ability. Collets 600, 700 can be made manufactured as disposable or they can be machined for several uses. The disclosed collets 600, 700 or variations thereof, in light of this disclosure, can be applied to coat any stent (metallic or polymer), and can designed to coat other tubular shaped medical devices (implantable coils, grafts, etc).

Returning again to FIGS. 5A, 5B, as mentioned earlier spindle 228 may be used to impart rotation to the mandrel assembly 222 during a spraying and/or drying operation. Spindle may also serve to impart intermittent rotations to the assembly 222 while the stent 1123 is restrained by grippers 250, 252 to break adhesion or re-position stent relative to collets as described earlier in connection with collets 1104, 600 and 700.

Figure 9:
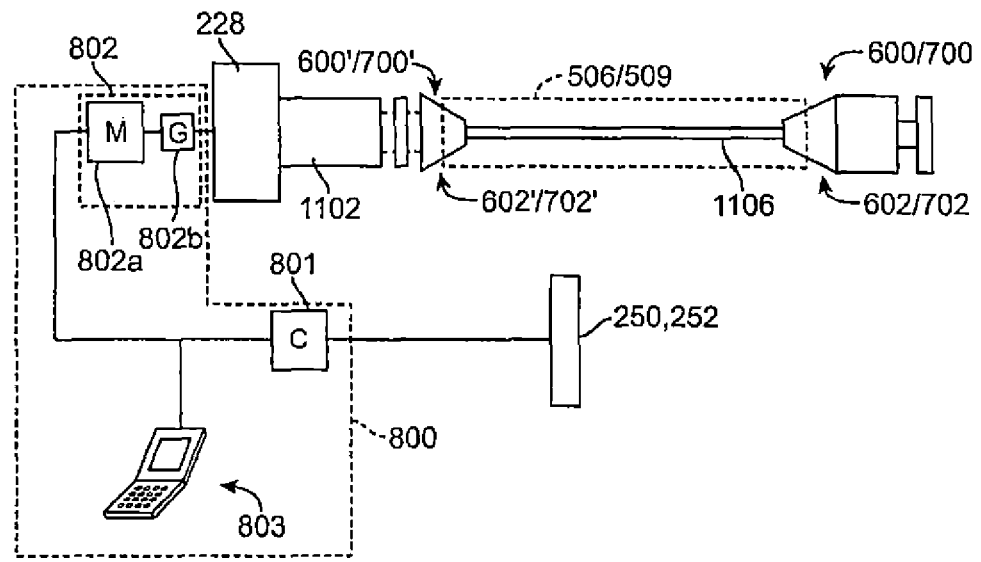
FIG. 9 illustrates a stent support system for controlling a mandrel assembly during and between spraying and drying cycles.

FIG. 9 illustrates a side view of mandrel assembly 222 according that may be used in connection with the second or third embodiments. FIG. 9 depicts a schematic illustration of a control system 800 for controlling rotation of the mandrel assembly 222 during spraying and drying cycles, and also between spraying and drying. As discussed earlier, spindle 228 is used to rotate the mandrel assembly 222 as the stent is placed in the spray and dry zones 202, 204 via rotating drum 248. Following a spray and dry cycle, the mandrel assembly 222 is disposed in the drying zone 204 and stationary. At this point, controller 801 initiates the gripper plates 252, 250 sequence to restrain the stent, e.g., stent 506 or stent 509. With stent restrained, controller 801 then initiates a programmed rotation of the mandrel assembly 222 via a motor 802 coupled to spindle 228. For example, the controller may cause spindle to rotate the mandrel assembly 222 back and forth to break up any adhesion between the stent and the collets, rotate through angles of 5, 10, 20, 30 or greater angles so as to place new stent crowns on the collet surfaces, etc. as discussed earlier. The sequence of rotations applied to the mandrel assembly 222 may be initiated automatically, following every spray and dry cycle, or at user-selectable times. Input parameters, which may depend on the type of stent (i.e., length, number of crowns, etc.), type of collet (e.g., collet 1104, 600 or 700) and weight of coating applied, can be supplied via a user interface 803 before the process of spraying and drying begins. Motor 802 may be any suitable motor 802A with a gear reduction 802B between it and mandrel assembly 222, or motor 802 may correspond to a stepper motor, which can provide highly precise rotational motion.

EXAMPLE

Figure 17C:
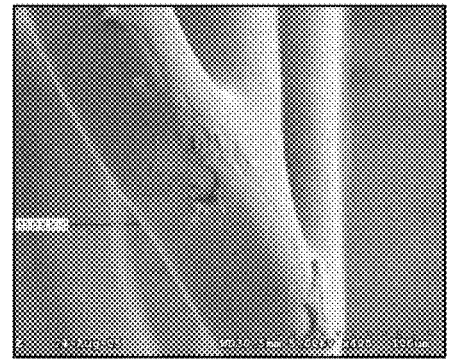
FIGS. 17A, 17B, and 17C show views of a stent that was coated while supported on collets according to the third embodiment.
Figure 17A:
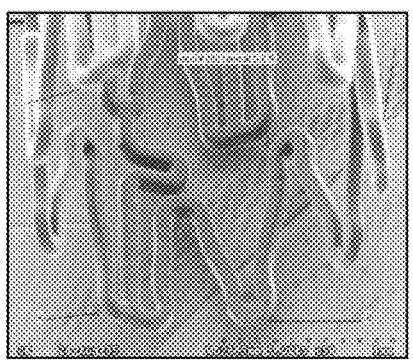
Figure 17B:
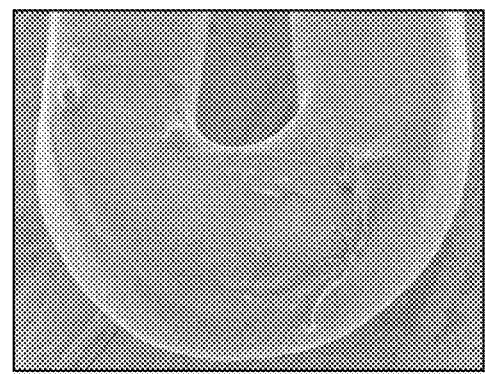

A mandrel having a pair of collets 700 (without a channel 702) supported a 18 mm Xience V stents (medium design). The members or lobes of the collets each had a width D of 0.039 inches to 0.046 inches. The stent-contacting surfaces of the collet were treated with a COMCO Micro Blaster before assembly of the mandrel. The stent was then loaded on the mandrel. The stent was mounted in such as manner as to allow relative rotation motion between coatings. The coating process included the following parameters: IVEK pump rate at 190 microsteps; unidirectional 35 deg clocking of the collet relative to the stent between coatings; drying nozzle temperature at 45 degrees Celsius (at stent's site) and drying air flow (MKS) set a 113 liter/min; and set the total spray pass at 30 and start coating cycles. FIGS. 17A-C are 400× magnification images of the stent for a coating weight of 600 micro-grams. FIG. 17A shows no detectable internal diameter defect. End ring defects were also negligible (FIGS. 17B-17C).

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for forming a coating on a stent, the method comprising:
   spraying or drying a coating on the stent while the stent is supported on a mandrel assembly, the stent having a first end, the stent supported such that a first part of the stent at the first end is in contact with the mandrel assembly; and
   during the spraying or drying, making the first part of the stent go out of contact with the mandrel assembly by vibrating the mandrel assembly.

2. The method of claim 1, wherein a coating adhesion between the first part of the stent and the mandrel assembly is broken when the first part of the stent goes out of contact with the mandrel assembly.

3. The method of claim 2, wherein the first part of the stent goes out of contact with the mandrel assembly during the drying, the drying including passing heated gas over the stent while the stent is supported on the mandrel assembly.

4. The method of claim 3, further comprising, before the drying, spraying the coating on the stent while supporting the first end of stent on the mandrel assembly.

5. The method of claim 4, further comprising, after the drying, spraying the stent with a second layer of coating while supporting the first end of the stent on the mandrel assembly, the second layer forming a second coating adhesion between a second part of the stent and the mandrel assembly.

6. The method of claim 5, further comprising making the second part of the stent go out of contact with the mandrel assembly by vibrating the mandrel assembly, wherein the second coating adhesion is broken when the second part of the stent goes out of contact with the mandrel assembly.

7. The method of claim 1, wherein the first part of the stent goes out of contact with the mandrel assembly during the spraying.

8. The method of claim 7, wherein the spraying is performed while the stent is being rotated by the mandrel assembly.

9. The method of claim 8, further comprising, after the spraying, drying the coating on the stent by passing heated gas over the stent while the first end of stent is supported on the mandrel assembly.

10. The method of claim 9, further comprising, during the passing of heated gas over the stent, making a second part of the stent go out of contact with the mandrel assembly by vibrating the mandrel assembly, wherein a coating adhesion is broken when the second part of the stent goes out of contact with the mandrel assembly.

11. The method of claim 1, wherein during the spraying or drying, the first part of the stent is in contact with at least one of a plurality of surfaces of the mandrel assembly, which surfaces together form a partial conical shape.

12. The method of claim 11, wherein each one of the plurality of surfaces includes a channel.

* * * * *